(12) United States Patent
Barakat (10) Patent No.: US 8,935,934 B2
(45) Date of Patent: *Jan. 20, 2015

(54) MONITORING TEMPERATURE-SENSITIVE CARGO WITH AUTOMATED GENERATION OF REGULATORY QUALIFICATION

(71) Applicant: TCP Reliable, Inc., Edison, NJ (US)

(72) Inventor: Maurice Barakat, Short Hills, NJ (US)

(73) Assignee: TCP Reliable, Inc., Edison, NJ (US)

( * ) Notice: Subject to any disclaimer, the term of this patent is extended or adjusted under 35 U.S.C. 154(b) by 22 days.

This patent is subject to a terminal disclaimer.

(21) Appl. No.: 14/096,442

(22) Filed: Dec. 4, 2013

(65) Prior Publication Data

US 2014/0352334 A1 Dec. 4, 2014

Related U.S. Application Data

(63) Continuation-in-part of application No. 13/794,952, filed on Mar. 12, 2013, now Pat. No. 8,696,151.

(51) Int. Cl.
    *F25B 49/00* (2006.01)
    *G05D 23/00* (2006.01)
    *F25D 31/00* (2006.01)

(52) U.S. Cl.
    CPC ................................. *F25D 31/006* (2013.01)
    USPC ........................ 62/129; 62/157; 414/222.02

(58) Field of Classification Search
    USPC ................. 62/62, 127, 129, 157, 231, 457.9;
        236/44 C, 46 C, 51, 91 C; 414/222.02;
        705/330, 341
    See application file for complete search history.

(56) References Cited

U.S. PATENT DOCUMENTS

| | | | |
|---|---|---|---|
| 6,865,516 | B1 | 3/2005 | Richardson |
| 7,294,374 | B2 * | 11/2007 | Romero .................... 428/34.1 |
| 7,350,703 | B2 | 4/2008 | Ambartsoumian |
| 7,630,864 | B2 | 12/2009 | Shoenfeld |
| 7,990,270 | B2 | 8/2011 | Mostov |
| 8,047,432 | B2 | 11/2011 | Breed |
| 8,192,924 | B1 | 6/2012 | Barakat et al. |
| 8,334,781 | B2 | 12/2012 | Heck et al. |
| 8,349,552 | B2 | 1/2013 | Haarmann et al. |
| 8,375,730 | B2 | 2/2013 | Haarmann et al. |
| 8,502,645 | B2 | 8/2013 | Thomas et al. |
| 8,520,900 | B2 | 8/2013 | Rhoads et al. |
| 8,696,151 | B1 * | 4/2014 | Barakat ..................... 362/129 |

(Continued)

FOREIGN PATENT DOCUMENTS

| | | |
|---|---|---|
| WO | WO0175700 A1 | 10/2001 |
| WO | WO2005062216 A1 | 7/2005 |

(Continued)

*Primary Examiner* — Marc Norman
(74) *Attorney, Agent, or Firm* — Eric P. Mirabel (57) ABSTRACT

Disclosed is a process of determining, at a point during shipment, whether the solid phase refrigerant in a shipment is sufficient to preserve the shipment cargo, which is blood or other biological products, for the remaining shipment period, by: monitoring the temperatures encountered to said point and estimating the temperatures likely to be encountered during the remaining shipment period; determining the likelihood that the remaining refrigerant can maintain the shipment cargo within a specified temperature range during the remaining shipment period; and if the risk that the remaining refrigerant cannot maintain the shipment cargo within said range during the remaining shipment period is above a cut-off level, then taking action to preserve the value of the cargo.

19 Claims, 4 Drawing Sheets

(56) References Cited

U.S. PATENT DOCUMENTS

| | | |
|---|---|---|
| 2004/0212509 A1 | 10/2004 | Zweig |
| 2007/0193297 A1 | 8/2007 | Wilson |
| 2008/0052044 A1 | 2/2008 | Shoenfeld |
| 2009/0293524 A1 | 12/2009 | Vezina et al. |
| 2010/0328037 A1 | 12/2010 | Thomas et al. |
| 2011/0022532 A1 | 1/2011 | Kriss |
| 2011/0163850 A1 | 7/2011 | Bachman et al. |
| 2012/0197810 A1* | 8/2012 | Haarmann et al. ............ 705/302 |
| 2013/0144724 A1 | 6/2013 | Ramer et al. |
| 2013/0245991 A1* | 9/2013 | Kriss ............................ 702/150 |
| 2013/0265139 A1 | 10/2013 | Nummila et al. |

FOREIGN PATENT DOCUMENTS

| | | |
|---|---|---|
| WO | WO2005062903 A1 | 7/2005 |
| WO | WO2012052604 A1 | 4/2012 |

* cited by examiner

Fig. 3

MONITORING TEMPERATURE-SENSITIVE CARGO WITH AUTOMATED GENERATION OF REGULATORY QUALIFICATION

FIELD OF THE INVENTION

The invention relates to monitoring shipment of blood and other temperature-sensitive biological products.

BACKGROUND OF THE INVENTION

Shipment of blood and perishable biological materials is problematic because of the short effective life of these products, and their high value. In general, insulated containers in combination with temperature-control agents, such as refrigerant materials, are widely used as a cost-effective system to maintain the temperature of shipped products at selected temperature ranges, including refrigeration (2-8° C.); room temperature (20-30° C.); or frozen (below 0° C.). The temperature-control agents are generally phase change materials, ice, gel packs, or dry ice.

Phase change materials are materials which may be repeatedly converted between solid and liquid phases and utilize their latent heats of fusion to absorb, store and release energy to heat or cool during such phase conversions. In contrast to a material that absorbs and releases energy essentially uniformly over a broad temperature range, a phase change material absorbs and releases a large quantity in the vicinity of its melting/freezing point, thus facilitating temperature maintenance near the melting/freezing point.

Passive refrigerant systems utilizing insulated containers and phase change materials (and/or ice, gel packs, or dry ice) provide sufficient refrigeration for relatively short shipping periods, where, as an additional condition, the ambient temperature does not vary greatly from the internal temperature for extended periods. As shipment times are often longer than the period where ice in an insulated container will melt completely, refrigerant systems using combinations of phase change materials, gel packs and insulated containers are commonplace for shipment of temperature-sensitive products. See, e.g., U.S. Pat. Nos. 7,849,708; 7,294,374 and 8,375,730 (all of which are incorporated by reference). Other systems of insulated containers and phase change materials can be used to extend the time that products within are maintained at room temperatures or at temperatures below freezing (and the latter systems may also include ice or gel packs or dry ice, as appropriate), so as to match the shipment period and the shipment conditions (most importantly, the ambient temperature). See U.S. Pat. No. 8,375,730 (incorporated by reference).

One issue which has not been addressed is how to best retain the value of blood and other perishable products during shipment. Units of whole blood and red blood cells are kept refrigerated at (1-6° C.), with maximum permitted storage periods (shelf lives) of 35 and 42 days respectively. Platelets are typically pooled before transfusion and have a shelf life of five days—or three days, assuming it takes two days following collection to complete their testing. Platelets are stored at room temperature (22.2° C.) and must be rocked. If there are significant temperature excursions during shipment of blood and biological products, it renders these products unacceptable for medical uses and thus valueless.

Thus for shipping blood and biological products with passive refrigerant systems, sufficient refrigerant must always be present to maintain the required storage temperature. The ambient temperature significantly affects the conversion rate of the refrigerant, and thus the time blood and biological products can be in shipment before an unacceptable temperature excursion takes place (which is one where the temperature is above a threshold for a given period; such that the higher the temperature, the shorter the given period before spoilage).

Time in shipment can only be estimated, as there are many sources of delay during shipment, both conventional and unexpected. Also, the temperature during shipment can only be estimated based on expected weather conditions and knowledge of shipment mode internal temperatures and warehouse temperatures. If a shipment of blood or biological products is delayed, and/or the temperature varies beyond expectation during shipment for more than a prescribed period, it is important to determine how much time is left before a sufficient quantity of the refrigerant is converted to cause an unacceptable temperature excursion. For blood or biological products, it is also important to have verification of appropriate shipping conditions (esp. temperature) for regulatory compliance purposes, for both the recipient and the shipper.

SUMMARY

The invention relates to a first embodiment for preservation of value in biological products and other perishable items, by using a logger of time/temperature (or real time RF transmission of time/temperature) so as to allow determination of the amount of refrigerant remaining, during shipping of the products. The invention also relates to a second embodiment for automated qualification of biological products and other perishable items or material shipped. In this second embodiment, a time/temperature logger shipped with the materials has a coding function to identify the materials shipped (for example, using a bar code) and a certificate coded to the materials and operatively associated with the logger carries an authentication of the time/temperature log which can be used in certifying that the materials shipped are suitable for intended use (though solely from a time/temperature exposure standpoint). Preferably, this certification carries all information needed for an NTIS (National Technical Information Service) compliant certification, and so can be used to satisfy requirements in the medical, blood banking, biotech and pharma industries for the shipment certified. The logger can also have other features useful for logging time/temperature and alerting an operator and certifying the shipment quality, as described further in the Detailed Description.

The first embodiment is accomplished by monitoring of the shipping system temperatures during shipment and the period of time at various temperatures, and from that information and the characteristics of the shipping system, deriving the amount of refrigerant remaining. Then, the temperatures (and preferably the humidity), and the time period at such temperatures (and preferably at each such humidity) to be encountered are predicted (from a database of logged shipments or from forecasts) and a determination is made of how long the remaining refrigerant can sustain the products within the required temperature range. The determination of how long the remaining refrigerant can so sustain the products depends on determining the relationship between the external predicted temperatures and humidity and the time at each such temperature or humidity, and the temperature within the shipping container which houses the product and the time the product is at such temperature. The temperature within the shipping container (when at a constant ambient temperature) will change as more refrigerant is consumed, until finally reaching equilibrium with the ambient temperature. A larger temperature gradient between interior and ambient will, of course, result in more rapid consumption of the refrigerant, as will longer time periods at higher temperatures.

After the remaining refrigerant quantity is determined, if the level is unsuitable or unsafe for the remaining shipment period, action can be taken, including moving the shipment to a faster transportation mode, instructing the shipper to add refrigerant, or diverting the shipment or moving the container (if it is in a warehouse) to a temperature-controlled environment (e.g., a refrigerated unit or a refrigerated cargo hold in a train, airplane or truck). The action taken might also be diverting the shipment to a nearby facility where the biological products can be used on site more immediately than originally planned. The monitoring and prediction described herein therefore allows one to take action to retain the value of biological products as the refrigerant level drops and shortens the effective life of the products. The automated qualification certificate described herein increases the practicality of diverting the shipment to a different location than originally planned, as the new location has a certification that the product it receives is qualified for the end use. The automated qualification also shows the recipient if the attempts to preserve the shipment were successful.

In the invention, first a suitable container and refrigerant system for products requiring maintenance within a specified range of temperatures during shipment (including blood, blood products and other biological products, for example, cells, tissues, organs, microbes, microbial spores, yeast, plants and plant materials) is selected based on estimated shipping time and temperatures expected to be encountered during shipping. The process requires a prediction of the maximum period of shipment, and the predicted ambient temperature ranges and time of exposure thereto for the system during the maximum period of shipment. Alternatively, instead of predicting ambient temperature ranges for the system and time of exposure thereto, a postulated worst case scenario for ambient temperatures (winter and summer) and time of exposure thereto can be used. The lowest-cost system likely to accomplish the objective of preserving the cargo can be selected, as the monitoring of the shipment provides for taking corrective action if the system might fail to be adequate for the entire shipment period.

The "ambient temperature" of concern is the ambient temperature for the system—not the environmental ambient temperature. The ambient temperature for the system is the temperature inside the cargo area of the shipment mode (i.e., inside a truck-trailer, a train or an airplane cargo hold) or in a warehouse while in transit, as this temperature is what affects the conversion rate of the refrigerant. Of course, the environmental ambient temperature and humidity will affect the ambient temperature of the cargo area, unless the cargo area is actively temperature-controlled. The environmental ambient temperature and humidity will change as the system moves to its destination through environmental temperature fluctuations, thereby causing the ambient temperature in the cargo area to also fluctuate (again, unless it is temperature-controlled).

The system selected for shipping can include some combination of insulated container(s), phase change materials, and other temperature control agents such as ice, gel packs or dry ice. The selection can be done by an algorithm which, based on heat transfer characteristics of the system containers and melting characteristics of the temperature-control agents, identifies a system which is likely able to maintain the product temperature within the required range under the predicted conditions for the shipment period, as described in U.S. Pat. No. 8,375,730 (incorporated by reference).

Either experimentation, or derivation from the properties of the system components, can be used to establish a database for a variety of packaging and temperature-control systems. The database provides the length of time each member system in the database can maintain products within a specified range of temperatures, when the member system is exposed to specified ranges of ambient temperatures (and humidity) for specified time periods. The database may also provide historic information on environmental ambient temperature and humidity along different shipment routes, in different seasons. The database can be used in deriving the predicted temperatures ranges the system will be exposed to during shipment to a specified location over a predicted shipment period with a particular system, or these predicted ranges and exposure times can be entered by the operator. As noted, the system is to be monitored during shipment to ascertain the cargo ambient temperature and time of exposure thereto, and preferably, there is also monitoring of the system's internal temperature during shipment—in order to verify the predictions, supplement the database, and provide protection for the products in case of temperature excursions exceeding specified periods. A logger which can perform such ambient temperature and/or cargo ambient temperature logging is described in the Detailed Description below.

As noted above, an alternative to predicting ambient temperatures and the shipment period is to establish worst case scenarios—i.e., the predicted boundaries of the temperature range(s) in summer and winter, and the maximum predicted period of shipment/exposure based on destination and mode of shipment selected. Then, a system is selected which will maintain the products within the required temperature range under these conditions; and it will necessarily also do so under generally-encountered shipping conditions. Again, monitoring of the ambient and system internal temperatures during shipment can be used in conjunction with such predictions to ascertain whether the products remain in an acceptable temperature range during shipment.

With respect to shipment of blood from donors, for direct donation and/or for processing into blood products, currently, Fresenius HemoCare (Redmond, Wash., USA) offers two cooling and transport systems for blood bags: Compocool, and a more recent version, Compocool II™/Compocool WB™, in which the butane-1,4-diol cooling unit is placed in an insulated crate. Additionally, Sebra/Haemonetics (Tucson, Ariz., USA) offers butane-1,4-diol-filled transparent pouches (ThermaSure), developed for the transport of platelet concentrates and blood units at 22±2° C. One of more of these cooling and transport systems, or other suitable blood cooling and transport systems (including those in U.S. Pat. Nos. 8,192,924; 8,349,552, both incorporated by reference), can be the cooling system selected in the method described herein for shipping of blood bags. In such case, the cooling and transport system (with the blood bags) would be placed into an insulated container, which may have additional temperature control agents.

Blood, organs for donation and other biological products must stay within a confined temperature range to be suitable for recipients. The selection method and monitoring described herein is particularly well-suited to selection of systems for blood and blood product shipment. Following shipment, the certificate automatically provides information about the suitability of the products based on temperatures they encountered and the times of such exposure. The products shipped can also be evaluated, assayed or tested following shipment to determine their donor compatibility or otherwise, and their suitability for in vivo or medical use.

The certification or verification of the cargo's integrity for regulatory purposes, which is done according to the second embodiment above, can be accomplished with conventional systems where a certificate is generated, or with one or more of the logger and/or sensor embodiments described below.

DETAILED DESCRIPTION

Goals and Qualification of Shipment System

Monitoring temperatures over time periods during shipment can be done with one of several commercial systems, including the Escort iMini™, the REDi Wireless™, and the Wireless Mini™, all made by Escort Dataloggers, Inc. (Buchanan, Va.). Data from these monitors can be viewed and plotted using the ESCORT Chartreader™. For the real time monitoring suitable for use with the systems herein (though not required for most systems), both the REDi Wireless™, and the Wireless Mini™ are suitable, as the data can be read or downloaded remotely.

To carry out the second embodiment without real time monitoring using RF or wireless transmission, the time/temperature logger shipped further needs a coding function to identify the materials shipped (for example, using a bar code) and data in the form of a certificate coded to the materials and operatively associated with the logger to authenticate the time/temperature log. For the second embodiment, the time/temperature logger must internally carry data for a certificate, and preferably, the logger will carry the data or a certificate itself in an all-device readable form (like Pdf), and preferably the logger can be directly plugged into a device port for reading the data or certificate (e.g. a USB port, where the logger has a USB male end, or another type of port, if the logger has another compatibility). With a USB or other port compatibility on the logger and an internal pdf for the data or the certificate, it can be plugged into a USB or other port of a smart phone or device that doesn't include a pdf reader program internally, and the data or certificate can then be read. More preferably, the logger will also include other features including for example those shown in FIGS. 3 and 4, and also as described in the section below "Logger and Sensor Embodiments".

In all embodiments, the time/temperature logger is used in an algorithm to predict the amount of refrigerant remaining, and the prediction of remaining shipment time and temperature determines whether action needs to be taken to preserve the value of the cargo—i.e., if the refrigerant is predicted to be insufficient to maintain the required temperature of the cargo. Over the course of shipment, the ambient temperature (i.e., the temperature the shipping container experiences) varies over time. The simplest case to ensure that the packaging system selected for shipment will comply with the time/temperature range restrictions for the products it carries, is to assume the ambient temperature range can be at the highest ambient summer temperature or at the lowest ambient winter temperature for the entire shipment period. Monitoring at selected points or intervals en route of the temperature and humidity encountered during shipment allows verification of the predicted conditions and allows determining the amount of refrigerant remaining, and allows tracking of product quality or expiration. The data logged can also be used to refine the database of predicted temperature over the route, for the season the shipment took place—thereby allowing continuous updating of such a database to make it more reliable. Determining the quality/expiry properties of shipped goods can be accomplished using loggers associated with particular shipment systems. In general, the logger can be inputted with a correlation or function which allows the computation of quality or expiration of cargo based on a correlation established between time of exposure and temperature, for such cargo, where the relationship is determined experimentally. Alternatively, the data for use in such correlation or function can be downloaded from the logger memory, and determined by another computing device. A number of functions exist for modeling degradation relationships including Arrhenius, Weibull, Eyring or Belehradek type functions. See U.S. Pat. No. 7,392,150, incorporated by reference.

In applying the Arrhenius equation to determine aging speed of a temperature-sensitive product (e.g. ageing speed=$1/e^{(a+b(temperature))}$, besides a knowledge of the good-specific constants, which are "a" and "b," a knowledge of the temperature over time is needed. This calculation provides a more accurate way to predict cargo quality and expiration than simply to monitor temperature and time values. If the algorithm result is monitored continuously (or at short, equal, intervals) during the monitoring period, then the quality determination is more reliable. The logger embodiments described in the section below "Logger and Sensor Embodiments" can run such algorithms and log the results, which can then either be transmitted wirelessly or uploaded to another device, also as described below.

Design of Shipment System

The first step in shipment of highly perishable goods is to select a suitable shipment system. The system can be selected based on lowest cost likely to accomplish the objective, as the monitoring of the shipment permits taking corrective action if the system selected proves inadequate. At various points or intervals during shipment, a determination of whether the remaining refrigerant is adequate can be made based on projecting the simplest case scenario (where one assumes the temperature range during shipment is either the highest likely or the lowest likely temperature) over the entire remaining shipment period.

The simplest case scenario can be segmented to represent exposure times to different ambient temperature ranges likely to be encountered en route. The total of these ranges and exposure times represent the ranges encountered during the shipment period and/or the remaining shipment period. Segmenting in this manner provides a more reliable prediction of the temperatures to be encountered during shipment. Again, at selected points during shipment, one can apply the segmented scenario to the remaining shipment period (designated $S_R$ in FIGS. 1 and 2), to determine if the remaining refrigerant is sufficient to sustain the required temperature during $S_R$.

As an example of segmenting during $S_R$: the system may begin its journey in a truck trailer without temperature control, then move to a temperature-controlled warehouse, then back to an uncontrolled truck trailer to finish its journey to the destination. If $S_R$ is determined, for example, after the truck trailer leaves the cargo in the temperature-controlled warehouse (before the final leg of the trip), then if $S^{TT}$ is the time remaining for shipment on a truck trailer, and if $s^W$ is the time the cargo is to remain in the warehouse, then $S_R = s^{TT} + s^W$. The prediction of ambient temperature range would then only be applied during $s^{TT}$ in determining whether the remaining refrigerant could sustain the cargo, as the ambient temperature during $s^W$ would be known.

As experience (actual data) is collected by loggers to determine the actual range of the ambient temperatures encountered, and the time of exposure to different temperature ranges on different shipment routes during different seasons, the temperature model can be modified, so that instead of applying the expected summer and winter high and low temperature (based on publicly available information) across $S_R$, values of summer and winter high and low temperatures closer to those likely to be experienced are substituted, and used with the expected times of exposure to these temperature ranges to determine remaining refrigerant over $S_R$. In the preceding scenario, during $s^{TT}$, if the temperature range applied in the model is based on experience rather than worst case, it will more reliably predict the amount of temperature-control agent likely to be consumed during $s^{TT}$.

The properties of shipment systems related to their ability to maintain the required inner temperature over the predicted ambient temperatures (especially heat transfer) are preferably tested or otherwise determined experimentally, and then the information is stored in a database. One testing method is to expose a series of systems to high temperatures and determine the melting time(s) for temperature-control agents inside. Another method of selecting systems is by derivation of expected temperature-control agent melting time(s) from the properties of the system's containers and temperature-control agents, at the predicted ambient temperature and time of exposure thereto.

In a preferred embodiment, during shipment, after monitoring the ambient temperatures and logging the results, a computer program (which can be in the logger internal programs) runs an algorithm to determine the remaining effective life of the temperature control agent(s), based on the properties of the shipment system, the temperature control agents, the ambient temperatures experienced and the ambient temperatures expected. The properties of the shipment system and the temperature control agents include the heat transfer characteristics of different systems (i.e., the heat transfer characteristics of both the temperature control agents and the container(s) in a system), and also the melting characteristics of the temperature-control agents. During shipment, therefore, the algorithm derives melt times and inner temperatures of different systems, and a logger can include enough indicators (see FIG. 3) to display (by coding) both whether the products on board are spoiled/unsafe for use, and whether the system can maintain the required product temperature for the remaining shipment period at the expected temperatures.

Figure 1:
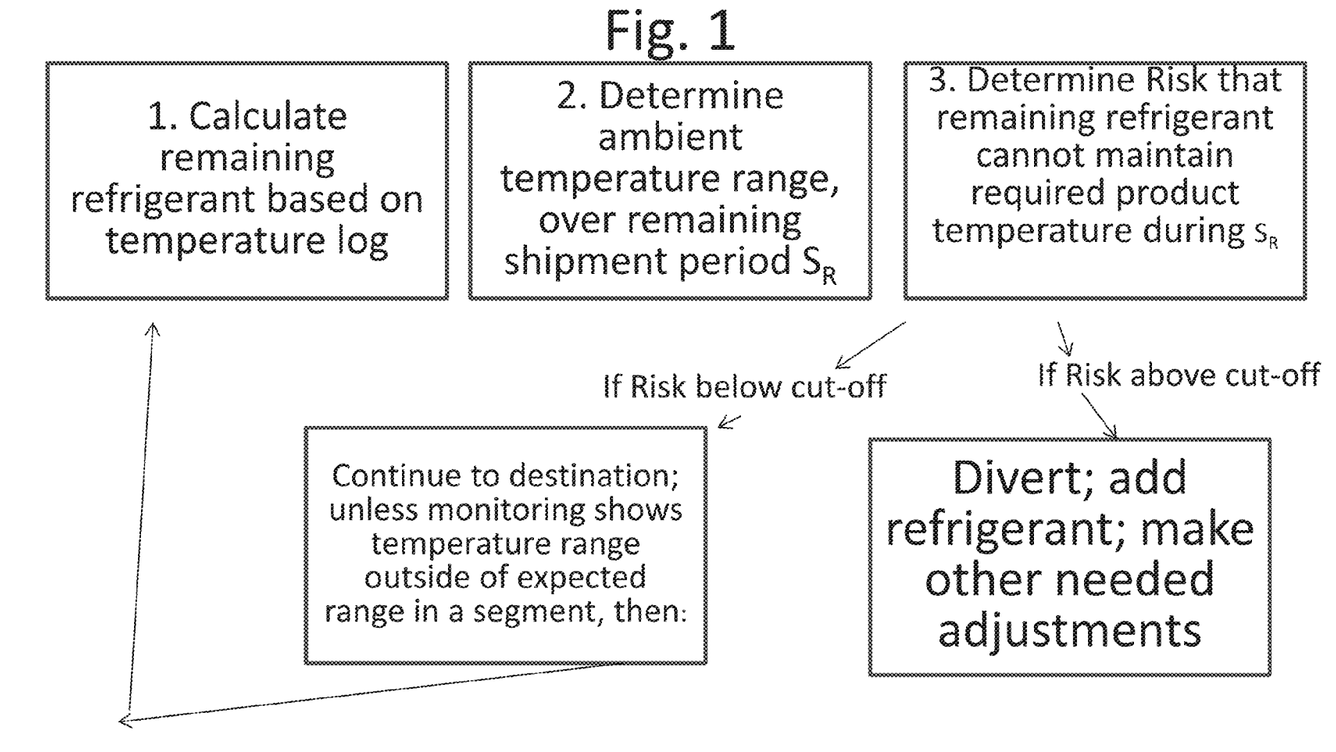
FIG. 1 is a flow diagram showing the steps in determining whether the product being shipped should be diverted, have refrigerant added, or be moved to a refrigerated area, where the assumed temperature range over the entire remaining shipment period $T_R$ is determined then applied. Where continued monitoring shows temperature excursions outside of expected ambient temperature range, the determination needs to be repeated based on the updated information.
Figure 2:
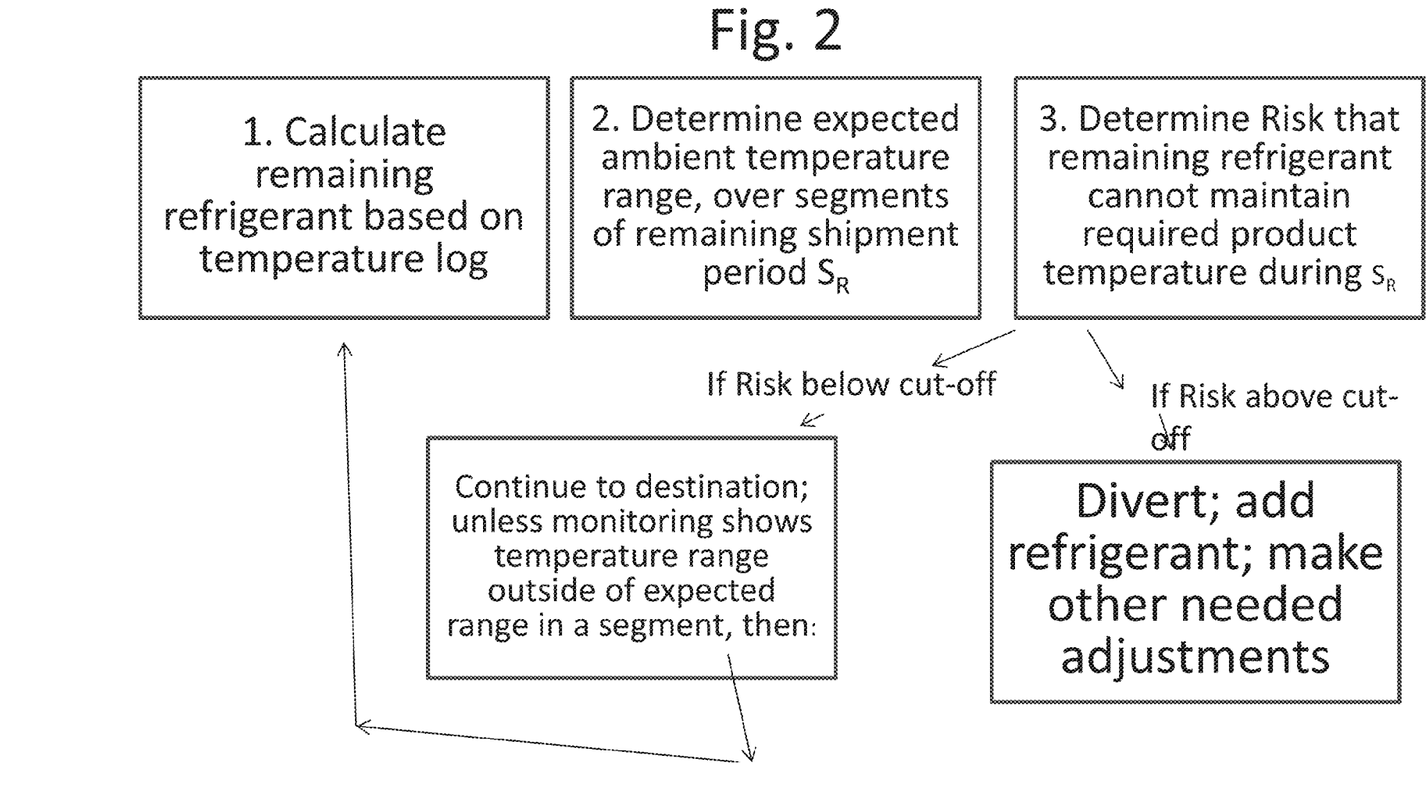
FIG. 2 is a flow diagram showing the steps in determining whether the product being shipped needs to be diverted, have refrigerant added, or be moved to a refrigerated area, where the assumed temperature range over a plurality of segments of the remaining shipment period $T_R$ is determined then applied. Where continued monitoring shows temperature excursions outside of expected ambient temperature range, the determination needs to be repeated based on the updated information

The situation where the remaining shipment period is segmented is shown in FIG. 2; and the non-segmented case is in FIG. 1. The ambient temperature applied by the algorithm can be the simplest case projection (a range from expected summer highs to winter low temperatures over the shipment route for the shipment period) or the segmented ranges and their respective times experienced. The ambient temperatures in the database can be updated and supplemented based on those actually experienced by systems, or, updated based on derived ambient temperatures resulting from the environmental ambient temperatures logged or predicted. The algorithm in a logger can also indicate the standard deviations in temperatures and shipment times, along different points in the route. This can allow an operator receiving information from the logger to determine the risk of unacceptable temperature excursions during the remainder of the shipment, and based on that calculation of risk, instruct action to preserve the cargo (as indicated in FIGS. 1 and 2). Again, the information can be received wirelessly or by downloading it from the logger.

A database of environmental temperatures along shipment routes (from which ambient temperature can be derived) can be established by compiling the historical temperature records for the route, or by actual monitoring, or by a combination of historical data and actual monitoring. In providing for the widest safety margin, one would determine the highest summer temperatures and the lowest winter temperatures ever recorded, and then derive ambient expected temperature from those extremes—preferably with a standard deviation for each. The expected ambient temperatures (from the database) can be in a computer or device for processing, and also could be loaded into a logger memory for processing when it is to determine if the remaining refrigerant is adequate.

On the other hand, if a shipper can warranty certain ranges of ambient temperatures for the remaining shipment period (i.e., climate controlled shipment and warehousing, from start to finish), there is no need to estimate the expected environmental ambient temperature. Where there is active monitoring of temperature and humidity as described herein, the key to preservation of the product shipped at a point during shipment is to ensure there will be no delays during the remaining shipment period—which the shipper may also warranty. If delays are expected, or if the shipper will not provide a warranty, action can be taken to preserve the cargo (as indicated in FIGS. 1 and 2). In the event of such warranty, however, the logger is still needed or useful to the recipient, as it verifies and can be used to certify the quality of the products shipped.

As noted, the time/temperature and time/humidity data logged from shipments can be added to the database, which is preferably done automatically. As the database expands, the predictions of the temperature ranges during various segments of shipment along routes where more data has been accumulated should become more reliable and deviations should narrow. The loggers with the shipments thus allow expanding and verifying a database, and generating a more reliable determination of which system (lowest cost) to select, and further, of when action is needed to preserve the shipment.

The temperature, humidity (and optionally related conditions that may affect temperature-control agent melting like atmospheric pressure) should be collected from the logger at multiple points during shipment. These datapoints can be used to construct a cold chain map. The map is preferably plotted at different times of the year to form a series of season-specific cold chain maps. These season-specific cold-chain maps can be used to derive a more accurate prediction of the temperatures the system would be likely to experience during any particular shipment segment.

The data on temperature during shipment can be collected using datalogging devices which are analyzed after or during shipment, or with the devices which transmit time/temperature data to a monitoring station (using RF transmission) throughout shipment. Both types of devices are available from Escort Data Loggers, Inc., Buchanan, Va. Actual monitoring or logging of temperature changes may be needed for customer assurance, or to meet the FDA GMP requirements, if the products are subject to FDA jurisdiction, for example, pharmaceuticals, biological products or blood products. The loggers described herein track and log the temperature automatically during shipment, and the temperature log is also automatically documented—which is necessary for many FDA regulated products and where documentation is part of the standard operating procedures (SOPs) for products.

A database also includes heat transfer characteristics of the system constituents, including the containers. The materials forming the containers are typically conventional materials used in fabricating portable coolers, e.g., expanded polystyrene or polyethylene, because of their insulating properties. The database also includes melting characteristics of a variety of phase-change materials and coolants which can be included in the packaging, as well as melting characteristics of a number of combinations of packaging and phase change materials and/or coolants. The algorithm used to determine whether the system can maintain the cargo for the remainder of the shipment period $S_R$, can display several alternative scenario based on expectations, and an operator can select one which best satisfies the needs in a particular case:

1. Determine if the system can meet the worst case temperature range for $S_R$ (FIG. 1).
2. Determine if the system can meet the time-segmented temperature ranges for $S_R$ (FIG. 2).
3. Determine if the system can meet the worst case or time-segmented temperature ranges for $S_R$, where the temperature ranges are based on historic data and/or weather forecasts for the shipping route.
4. Determine if the system can meet the worst case or time-segmented temperature ranges for $S_R$, where the temperature ranges are based on historic data and/or weather forecasts for the shipping route and/or on data collected during shipment on the route.
5. For systems meeting the criterion in any of scenarios 1 to 4 above, determine the risk of cargo destruction due to temperature excursions/refrigerant conversion for each scenario; and
6. Where risk is above a cut-off level (where the cut-off level is based on cargo value) select a system (likely higher cost) which is more likely to preserve cargo value; or, be prepared to respond en route (based on the results of monitoring with the logger) with action to preserve the cargo value.

En Route Response to Unacceptable Cargo Risk

Having selected a shipping system based on the criteria above, as noted in factor 6 above, monitoring of time/temperature allows responses en route to preserve the cargo value. The cut-off level for the risk level (in factor 6) can be pre-set, and would be lower where cargo value was higher. The cut-off level could also be graded depending on the action to be taken, and its feasibility. For example, it may not possible to "add refrigerant" to the shipping system, in locations or on routes where no suitable refrigerant (typically a phase change material) is readily available. It may also not be possible to divert the shipment to have the cargo used within its remaining effective life. No proximate facility may be willing to purchase/take the cargo. Thus the action to be taken in such cases could only be "expedite shipment," which is likely the most costly alternative to preserve the cargo value. Such relative costs can be taken into account by setting or re-setting the basic risk cut-off level—i.e., the risk can be re-set to a higher level if only higher-cost alternatives are available, meaning a system which has a prospect for longer cargo preservation is preferred. Of course if the cost of action is greater than the value of the cargo to be preserved, that can be built into the calculation as a limitation on further action. It is also possible to have communication with the customer about the course of action to be pursued, and to obtain their direct approval for any action to be taken. In any event, monitoring by the logger during shipment allows the risk to the cargo during the remainder of the shipment to be more accurately assessed—as its exposure to such point would be better quantified.

The different courses of action to preserve the cargo value and their costs can be programmed as an algorithm, and the lowest cost alternative can be determined by the algorithm. Again, this could be performed by the logger with an internal function, if desired.

Logger, Certificate and Sensor Embodiments

Monitoring systems available from Escort Data Loggers, Inc. allow transmitting data regarding temperature, and also pressure, relative humidity, and $CO_2$ levels, using RF, other wireless modes or WiFi. Other monitoring systems available from Escort Data Loggers, Inc. keep an internal record of temperature and time of exposure, in the logger device memory. If a GPS system is included with the device, it allows locating the system at the time data is recorded or sent/received. Indicators which can be monitored indicate temperature excursions, and are preferred where maintaining product temperature is critical; i.e., for blood or other biological products. The data logged internally on time/temperature or transmitted is preferably also recorded and preserved on a database, which is preferably web-accessible. As noted, this database and monitoring system can be used to verify or refute predicted temperatures, to establish or supplement a cold chain map along different shipment routes, and most importantly, to establish the effective amount of the remaining refrigerant and determine if it will be effective over the expected remaining shipment time.

Figure 3:
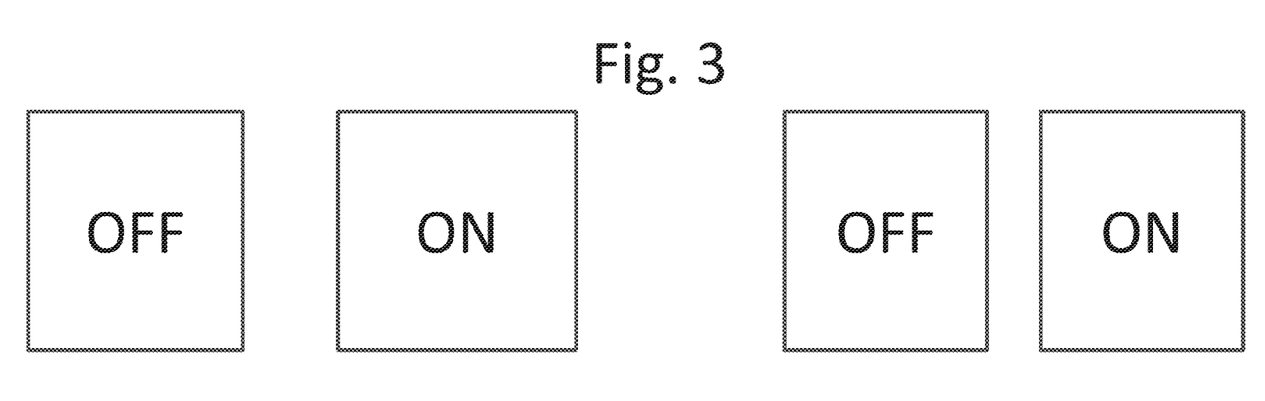
FIG. 3 depicts four LED indicators on a logger, with two for indicating high temperatures (the left most indicators) and two for low temperatures (the right most indicators). One each of the high temperature and low temperature indictors is depicted as being on in FIG. 3.

The logger system described below and shown in FIG. 3 is a suitable lower-cost alternative to the foregoing systems which transmit data. This logger has four or more LEDs which indicate time/temperature, and therefore status of the cargo. One system of coding the four LEDs is to split them so that two which signal in one color indicate high temperature and two which signal in another color indicate low temperature. Then, temperatures above an uppermost limit for a specified period can be indicated by activating two high signals, and temperatures above a limit lower than the uppermost for a specified period can be indicated by activating one of the high signals only. Similarly, temperatures below a lowermost limit for a specified period can be indicated by activating two low signals, and temperatures below a limit higher than the lowermost for a specified period can be indicated by activating one of the low signals only.

The FIG. 3 logger is shown with only one left-hand indicator on, indicating the temperature was above a primary high threshold for a specified period. The FIG. 3 logger is also shown with only one right-hand indicator on, indicating the temperature was below a primary low threshold for a specified period as well. Such indicator arrangement as in FIG. 3 can provide a quick visual indication of the cargo status, and where the signals are designed to remain on, the indication of cargo status can be viewed at the destination. A number of patents discuss loggers which keep signals on without consuming excess battery power, and are hereby incorporated by reference: e.g., U.S. Pat. No. 7,392,150 refers to a low-energy consuming LCD for signal display (col. 4, line 37).

The preferred logger also includes all software needed to generate a certificate of time/temperature (preferably NTIS compliant) during shipment in pdf, excel or other readable format. The preferred logger can be connected to a USB port of a device, and the certificate can be read, without the need for having pdf- or excel reader software on the device; provided the device has conventional software, e.g., Android™. Thus, it can be read by tablets, smart-phones and other handheld or portable computing devices.

Having a certificate incorporated internally in the logger also is an advantage in that loggers can be pre-certified en masse, as operating correctly, prior to use. Normally, loggers must be pre-certified by testing them in a temperature controlled environment (a chamber) where the temperature is varied in a certain manner, and the logger is checked to determine if the logger recorded the temperature changes accurately. With the certificate incorporated, a number of loggers can be tested together, and then the certificates can be read together to verify correct functioning. In a further improvement, the certification reflects pre-programming which "knows" what the chamber temperature variation should be over time, and the certificate shows if the temperature variation in the chamber does not match the expected values—there is then a visible alert on the logger's certificate for that logger.

In yet another embodiment, the logger is a slave where the data logged can be read and recorded (and if needed analyzed) by a master computer. One convenient form of this embodiment has a male USB on the logger which plugs into the USB port on the computer. Preferably, as noted above, the logger, retains pdf, excel and other formats internally, so there is no need for the reader-device to have software to read such certificates (or other documents). Thus, these documents can be read by computers, tablets, smart-phones and other handheld or portable computing devices. The master-slave arrangement of loggers may be particularly preferred where different loggers are associated with different products in a refrigerator, freezer or climate-controlled condition during shipment. At selected intervals, one can take the data from the loggers to the master-computer, preferably through the USB port. This arrangement eliminates the need for and the greater expense of real-time RF transmission of time/temperature data (which further cannot be done for air cargo), as the monitoring at select intervals will be adequate to verify the reliability of the climate-control for each logger-associated product.

Another preferred embodiment for loggers includes LCD displays which are called Epaper™ (by E Ink Holdings Inc., Taiwan). They can retain black and white or color images (like bar codes, numerals, letters or Chinese characters) for extended periods (even years) with only the power of an internal mini-battery as the energy supply. The certificate itself and/or a bar code or other product or logger identifiers can be displayed on LCDs on the logger with this technology, and then read or reviewed by the operator at a later time.

Figure 4:
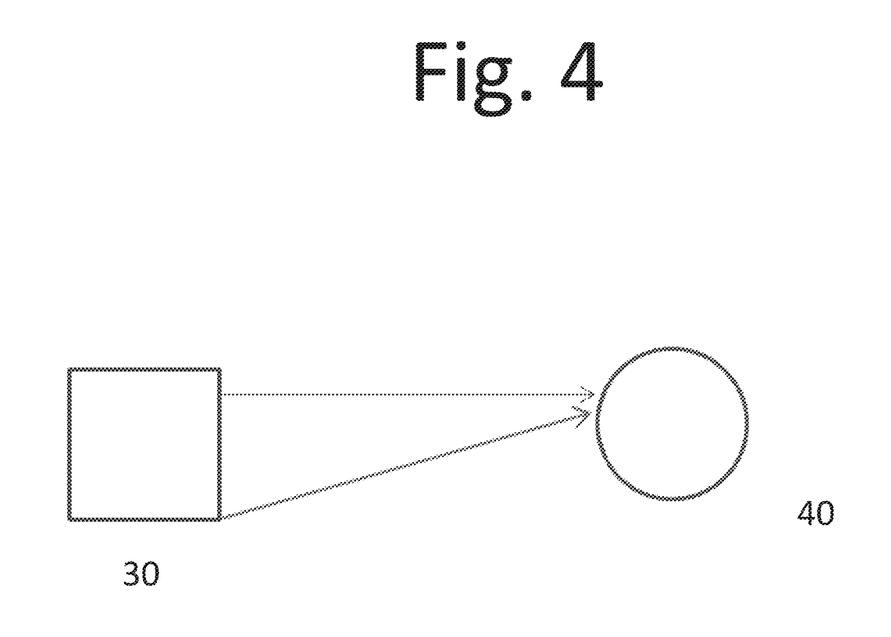
FIG. 4 depicts a logger (30) for attachment to a shipping carton (which can be an RFID logger); having multiple sensors (the arrows) with environmental probes designed to extend into a shipment carton to near the cargo (40).

In a particular logger embodiment, the logger can be associated with environmental sensors (including temperature, humidity or others) using circuits printed on paper with nanotechnology, as disclosed in US Publ'n No. 20110200873 (incorporated by reference). Such printed circuits would extend from a logger outside the box to the inside, or from a logger on the inside, out. The sensors would feed data back to the logger for recordation or analysis. Such a system is depicted in FIG. 4, where the logger 30 has sensors (arrows) extending to cargo 40.

Shipment Systems

An issue related to preservation of refrigerant is the initial selection of a shipment system. In that regard, U.S. Pat. No. 8,375,730 has such description and is incorporated by reference. This patent describes an algorithm for selection of a shipment system where expected temperatures, shipment duration and cost are considerations in selection. As noted, the preservation of the refrigerant is directly related to the heat transfer properties of the shipment system, and generally, more costly systems are better insulated and preserve refrigerant for longer periods (under the same conditions).

Preferred refrigerants are dry ice, ice, frozen gel packs or phase change material. Preferred phase change materials are 1-dodecanol and 1-decanol, and a particularly preferred combination has 98% 1-dodecanol, 1.5% myristyl alcohol and 0.5% 1-decanol, as disclosed in U.S. Pat. No. 8,192,924 (incorporated by reference).

In one embodiment, both system selection and monitoring of the shipment can be performed from a remote location. Such remote monitoring can be accomplished with either RF transmission of data or using one of the logger systems where data is stored and recorded in the logger, and then extracted using a computer or other reader (which results are fed to the remote location). In one modification of the method, the customer can perform the shipping system selection and/or shipment monitoring functions themselves, and then decide themselves whether to take action to preserve the shipment while it is en route (i.e., they can decide whether to move the shipment to a faster transportation mode, instruct the shipper to add refrigerant, or divert the shipment or move the system to a temperature-controlled environment).

To make a selection of an appropriate system, one may also need to monitor and establish the effect the ambient temperature has on the ice, gel packs or phase change material in each type of container which can be part of a system, over time. Alternatively, such effect can be derived from the heat transfer characteristics of the packaging and the melting time of the ice, gel packs or phase change material, and not verified by actual monitoring. A monitoring system which includes an alarm system for temperature excursions can alert the shipper or recipient that the phase change material or ice may be melted and needs to be checked. Again, action can be taken if needed or if the risk level of cargo damage is too high.

Segmenting the time of exposure (FIG. 2) to environmental ambient temperatures is particularly appropriate in cases where the ambient temperatures are unregulated during shipment, like in a truck trailer, but where the system spends a substantial part of the trip in a temperature-controlled environment (warehouse or temperature-controlled cargo hold). Segmenting in these cases helps protect against the effect of exposure to the unregulated ambient temperatures, but helps avoid over-compensating for the temperature extreme(s) during this exposure, and changing system requirements or taking action where there is no need to.

The containers for the system can be any of a number of designs and materials, including expanded polystyrene and polyethylene. Containers can also be multi-layered, one inside another, with one such arrangement shown in U.S. Pat. No. 7,849,708 (incorporated by reference), wherein an inner container includes a phase change material and the product, and an outer container includes gel packs. Various combinations of containers, gel packs, ice, dry ice and phase change materials are readily apparent to one skilled in the art. For example, one could have multiple containers layered within each other, with layers of different temperature-control agents in different quantities in different containers.

Phase change materials are relatively expensive, and thus one seeks to minimize their use, and substitute ice, gel packs, dry ice or container designs which add insulation, where feasible.

Phase change materials are not consumed in the cooling process, and can be re-frozen and used again. But a practical difficulty in re-use may be that the customer will not return the phase change material they receive—meaning it must be expensed with the rest of the system, which the customer would usually retain.

The real-time shipment monitoring disclosed herein allows selection of slower, lower-cost shipment options. The cost of the faster shipment options can be balanced against the likelihood that the system can maintain the product for the time required under slower shipment modes. Shipment cost may be lower when using slower shipment with monitoring, to protect the cargo even with such slow shipment.

At some point following arrival of blood/biological materials at the end-user destination, the materials would be tested to determine their suitability for use in patients or as reagents in assays or otherwise tested to determine their suitability for the purpose they were requested by the end-user. The effect of shipment on the products might be determined soon after arrival, or, their suitability for use in patients or as reagents may be tested well after arrival. In either case, a biological assay is performed on the products, which can be one or more of: an antibody-mediated assay including an enzyme-linked immunosorbent assay (See e.g., U.S. Pat. No. 8,021,850, incorporated by reference), a nucleic acid hybridization assay (See e.g., U.S. Pat. No. 8,036,835, incorporated by reference), an elongation-mediated chain terminating assay (U.S. Pat. No. 6,972,174 incorporated by reference), an elongation-mediated assay or a ligation assay (U.S. Pat. No. 7,262,032, incorporated by reference), a cell-based assay (U.S. Pat. No. 7,655,421, incorporated by reference) or a viability, blood-typing or tissue-type matching assay, including but not limited to an HLA-typing or a serological assay.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants. The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A process of determining, at a point during shipment, whether a solid phase refrigerant in a shipment is sufficient to preserve a shipment cargo, which is blood or other biological products, for a remaining shipment period to an intended recipient, comprising:
monitoring temperatures encountered and the time of exposure to such temperatures to said point by the shipment, using a logger which is connected to temperature sensors, and estimating temperatures likely to be encountered during the remaining shipment period and time of exposure to said estimated temperatures;
determining a likelihood that the remaining refrigerant can maintain the shipment cargo within a specified temperature range during the remaining shipment period based on the estimation of the temperatures likely to be encountered and the time of exposure; and
if risk that the remaining refrigerant cannot maintain the shipment cargo within said range during the remaining shipment period is above a cut-off level, then adding refrigerant to the shipment, moving the shipment to a faster transportation mode, moving the shipment to a temperature-controlled environment, or diverting the shipment to a different recipient.

2. The process of claim 1 wherein the temperature-controlled environment is a refrigeration unit or a refrigerated cargo hold in a train, airplane or truck.

3. The process of claim 1 further including establishing a database for a plurality of temperature-control systems, each system including containers for the solid phase refrigerant, wherein the database can be used to determine the length of time each member system can maintain products housed in the containers with the refrigerant within a specified range of temperatures when the shipment is exposed to specified ranges of ambient temperatures for specified time periods, and wherein the specified ranges and time periods represent, respectively, the predicted ambient temperature ranges and times of exposure thereto for the shipment during the shipment period.

4. The process of claim 3 wherein the database is established by deriving, from the characteristics of the containers and the refrigerants, the length of time each temperature-control system can maintain products housed in the containers with the specified refrigerants within a specified range of temperatures when the temperature-control system is exposed to specified ranges of ambient temperatures for specified time periods.

5. The process of claim 1 further including establishing a database for a plurality of shipment routes, at different times of the year, which reflects the different temperatures encountered en route for the shipment and the time of exposure for different temperatures.

6. The process of claim 1 further including testing the blood or biological products using a biological assay, which may be one or more of: an antibody-mediated assay; a nucleic acid assay; a cell-based assay; or a blood-typing or tissue-typing assay wherein, in the course of the assay, there is one or more of: nucleic acid hybridization, nucleic acid chain elongation, antibody-protein binding, or protein-protein binding.

7. The process of claim 1 wherein the solid phase refrigerants are dry ice, ice, frozen gel packs or phase change material.

8. The process of claim 7 wherein the phase change material is 1-dodecanol.

9. The process of claim 1 further including a GPS system to allow location of the shipment en route.

10. The process of claim 9 wherein the location and monitoring of temperatures can be performed from a remote location through a web-based system allowing computer access.

11. The process of claim 1 wherein the estimating of the temperatures likely to be encountered during the remaining shipment period is by determining the lowest ambient temperature likely to be experienced by the shipment to the highest ambient temperature likely to be experienced by the shipment.

12. The process of claim 11 wherein ambient temperature is monitored during shipment and indicators on a logger indicate excursions from the predicted ambient temperature range for greater than specified periods.

13. The process of claim 11 wherein the relative humidity, pressure and $CO_2$ is also monitored during shipment.

14. The process of claim 1 wherein the estimating of the temperatures likely to be encountered during the remaining shipment period is based on historic ambient temperature data for the predicted shipping route.

15. The process of claim 1 wherein the cost of different actions is determined.

16. A process of ensuring low cost shipment of biological products requiring temperature-control, comprising:
    determining a maximum predicted period of shipment for a biological product and predicted ambient temperature ranges during shipment and predicted time of exposure to each said ambient temperature range;
    selecting the lowest-cost system of containers and solid phase refrigerants likely to maintain the biological products within a specified range of temperatures during the shipment period;
    determining, at a point during shipment, whether the solid phase refrigerant is sufficient to preserve the biological products, for the remaining shipment period, by:
    monitoring the temperatures encountered and the time of exposure to such temperatures to said point by the shipment, using a logger which is connected to temperature sensors and which includes at least four indicators coded to reflect different temperature thresholds by illumination of different combinations of indicators, and estimating the temperatures likely to be encountered during the remaining shipment period; and
    determining the likelihood that the remaining refrigerant can maintain the shipment cargo within a specified temperature range during the remaining shipment period based on the estimation of the temperatures likely to be encountered;
    if the likelihood that the remaining refrigerant cannot maintain the shipment cargo within said range during the remaining shipment period is above a cut-off level, adding refrigerant to the shipment, moving the shipment to a faster transportation mode, moving the shipment to a temperature-controlled environment, or diverting the shipment to a different recipient.

17. The process of claim 16 wherein if the risk that the remaining refrigerant cannot maintain the shipment cargo within said range during the remaining shipment period is above a cut-off level, taking action to preserve the value of the cargo, including adding refrigerant to the shipment, moving the shipment to a faster transportation mode, moving the shipment to a temperature-controlled environment, or diverting the shipment to a different recipient.

18. The process of claim 16 wherein the logger further includes a record of all data on temperatures encountered and the time of exposure and a program to transform the data into a certificate representing the temperatures encountered and the time of exposure.

19. The process of claim 18 wherein the certificate is retained in a device-readable form by the logger after generation by the logger.

* * * * *